US010520454B2

(12) United States Patent
Strelec et al.

(10) Patent No.: US 10,520,454 B2
(45) Date of Patent: Dec. 31, 2019

(54) INNOVATIVE X-RAY SOURCE FOR USE IN TOMOGRAPHIC IMAGING

(71) Applicant: FEI Company, Hillsboro, OR (US)

(72) Inventors: Petr Strelec, Podoli u Brna (CZ); Ondrej Shanel, Vrbno pod Pradedem (CZ)

(73) Assignee: FEI Company, Hillsboro, OR (US)

( * ) Notice: Subject to any disclaimer, the term of this patent is extended or adjusted under 35 U.S.C. 154(b) by 290 days.

(21) Appl. No.: 15/585,059

(22) Filed: May 2, 2017

(65) Prior Publication Data
US 2018/0323032 A1 Nov. 8, 2018

(51) Int. Cl.
| | |
|---|---|
| *G01N 23/046* | (2018.01) |
| *G21K 7/00* | (2006.01) |
| *H01J 35/18* | (2006.01) |
| *H01J 35/08* | (2006.01) |

(52) U.S. Cl.
CPC ............ *G01N 23/046* (2013.01); *G21K 7/00* (2013.01); *H01J 35/116* (2019.05); *H01J 35/186* (2019.05)

(58) Field of Classification Search
CPC .......... G01N 23/046; G01N 2223/3035; H01J 2235/068; H01J 35/06; H01J 35/30; H01J 35/186; H01J 35/116; G21K 7/00
See application file for complete search history.

(56) References Cited

U.S. PATENT DOCUMENTS

| | | | |
|---|---|---|---|
| 6,377,660 B1 * | 4/2002 | Ukita ...................... | H01J 35/08 378/124 |
| 2008/0240344 A1 | 10/2008 | Reinhold | |
| 2009/0232270 A1 | 9/2009 | Okunuki et al. | |
| 2013/0301805 A1 * | 11/2013 | Hemberg ................ | H01J 35/08 378/137 |
| 2015/0092924 A1 * | 4/2015 | Yun ......................... | H01J 35/12 378/143 |
| 2015/0303021 A1 | 10/2015 | Parker et al. | |

FOREIGN PATENT DOCUMENTS

WO  2003081631 A1  10/2003

OTHER PUBLICATIONS

Laloum et al., "Deep sub micrometer imaging of defects in copper pillars by X-ray tomography in a SEM", Micron, vol. 58, pp. 1-8 (Year: 2014).*

(Continued)

*Primary Examiner* — Chih-Cheng Kao

(57) ABSTRACT

A method, target, and apparatus are disclosed for investigating a specimen using X-ray tomography. The specimen in mounted on a specimen holder. An X-ray target has a substrate of relatively low-atomic-number material carrying an array of mutually isolated nuggets of a relatively high-atomic number material. X-rays are generated by irradiating a single nugget in the target with a charged particle beam, which then illuminates the specimen along a first line of sight through the specimen. A flux of X-rays transmitted through the specimen is detected to form a first image. The illumination process is repeated for a series of different lines of sight through the specimen, to produce a series of images. A mathematical reconstruction on the series of images is then performed to produce a tomogram of at least part of the specimen.

16 Claims, 5 Drawing Sheets

(56) References Cited

OTHER PUBLICATIONS

Figure 1:
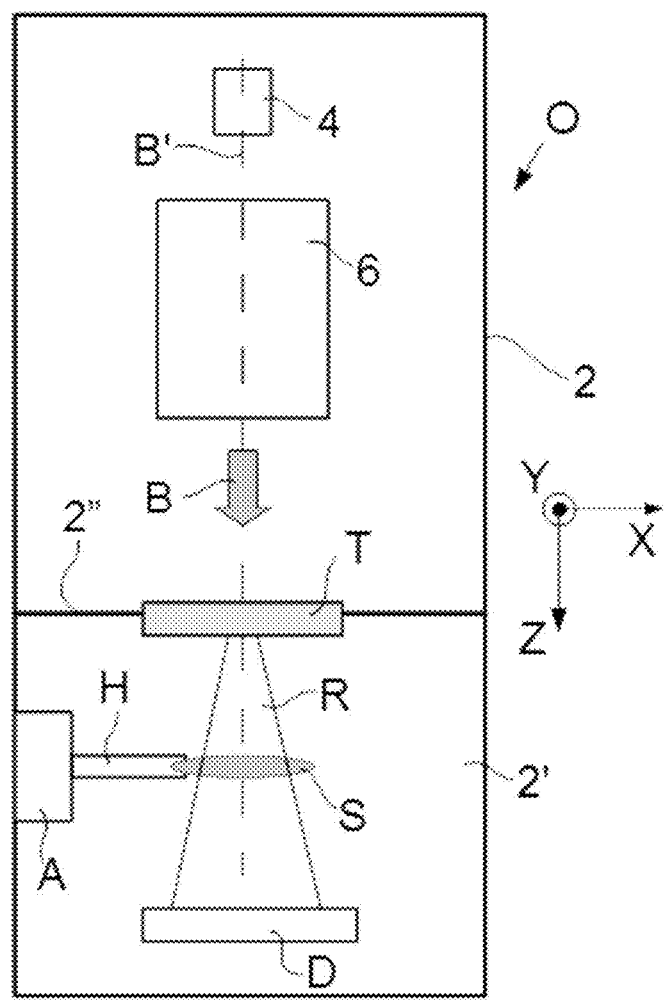

"Cone Beam Computed Tomography", Wikipedia, Retrieved from the Internet Aug. 4, 2016, https://en.wikipedia.org/wiki/Cone_beam_computed_tomography, 8 pages.
"Electron Microscope", Wikipedia, Retrieved from the Internet Oct. 15, 2015, http://en.wikipedia.org/wiki/Electron_microscope, 11 pages.
"Focused Ion Beam", Wikipedia, Retrieved from the Internet Jul. 11, 2016, https://en.wikipedia.org/wiki/Focused_ion_beam, 7 pages.
"Nanotomography", Wikipedia, Retrieved from the Internet Aug. 4, 2016, from https://en.wikipedia.org/wiki/Nanotomography, 1 page.
"Scanning Electron Microscope", Wikipedia. Retrieved from the Internet Jul. 25, 2016, http://en.wikipedia.org/wiki/Scanning_electron_microscope, 23 pages.
"Scanning Helium Ion Microscope", Wikipedia, Retrieved from the Internet on Jul. 25, 2016, http://en.wikipedia.org/wiki/Scanning_Helium_Ion_Microscope, 2 pages.
"Scanning Transmission Electron Microscopy", Wikipedia, Retrieved from the Internet Jul. 25, 2016, http://en.wikipedia.org/wiki/Scanning_transmission_electron_microscopy, 5 pages.
"Spiral Computed Tomography", Wikipedia, Retrieved from the Internet Aug. 4, 2016, https://en.wikipedia.org/wiki/Spiral_computed_tomography, 2 pages.
"Transmission Electron Microscopy", Wikipedia, Retrieved from the Internet Jul. 25, 2016, http://en.wikipedia.org/wiki/Transmission_electron_microscopy, 23 pages.
"X-Ray Microtomography", Wikipedia, Retrieved from the Internet Aug. 4, 2016, https://en.wikipedia.org/wiki/X-ray_microtomography, 5 pages.
Escovitz, W.H. et al., "Scanning Transmission Ion Microscope with a Field Ion Source," Proc. Nat. Acad. Sci. USA, May 1975, pp. 1826-1828, vol. 72, No. 5.
Neuser, E., et al. "NanoCT® Visualizing internal 3D structures with submicrometer resolution", DIR 2007, 18 p, vol. 39 Issue 41,International symposium on digital industrial radiology and computed tomography, France.
Rezvani, Nargol, "Reconstruction Algorithms in Computerized Tomography," CAIMS, 2009, 39 pages.
Varentsov, D. et al. "First biological images with high-energy proton microscopy", Physica Medica (2013), pp. 208-213, vol. 29.
Bleuet, P. et al., "SEM-based system for 100nm x-ray tomography for the analysis of porous silicon," Proceedings of SPIE, Sep. 11, 2014, vol. 9212, pp. 92120Z-1 to 92120Z-9.
Gomes Perini, L.A. et al., "Towards laboratory x-ray nanotomography: instrumental improvements on a SEM-based system," Proc. of SPIE, (2016), 7 pages, vol. 9967.

* cited by examiner

INNOVATIVE X-RAY SOURCE FOR USE IN TOMOGRAPHIC IMAGING

The invention relates to a method of investigating a specimen using X-ray tomography, comprising:
(a) Mounting the specimen to a specimen holder;
(b) Providing an X-ray source, in which X-rays are generated by irradiating a target with a charged particle beam;
(c) Using said X-ray source to illuminate the specimen with a beam of X-rays along a first line of sight through the specimen, detecting a flux of X-rays transmitted through the specimen and forming a first image therewith;
(d) Repeating step (c) for a series of different lines of sight through the specimen, thereby producing a corresponding series of images;
(e) Performing a mathematical reconstruction on said series of images, so as produce a tomogram of at least part of the specimen.

The invention also relates to an X-ray (generating) target for use in such a method.

The invention further relates to a tomographic apparatus in which such a method can be performed.

The invention additionally relates to a charged particle microscope in which such a tomographic apparatus is comprised.

In tomographic imaging (also referred to as Computed Tomography (CT)) as referred to above, the source and (diametrically opposed) detector are used to look through the specimen along different lines of sight, so as to acquire penetrative observations of the specimen from a variety of perspectives; these are then used as input to a mathematical procedure that produces a reconstructed "volume image" of (part of) the (interior of) the specimen. In order to achieve a series of different lines of sight as alluded to here, one can, for example, choose to:
(i) Keep the source and detector static and move the specimen relative to them;
(ii) Keep the specimen static and move the source relative to it. In this case, one can elect to:
  Move the detector in synchronization with the source; or
  Embody the detector as a (static) array of sub-detectors, with positions matched to correspond to the different positions to be assumed by the source.
(iii) Use a static, distributed array of sources/detectors—in conjunction with a static specimen—and invoke different source/detector pairs along different lines of sight, either serially or concurrently.

Regardless of whether the source or specimen is moved, it is possible to describe their relative motion using (for example) a specimen-centric coordinate system/reference frame. Typically, use is made of:
A circular scan, in which the source follows a planar orbit about the specimen, and images are captured at a relatively high sampling rate (i.e. quasi-continuously) along this orbit. This type of scan can be applied in situations where only a relatively thin "slice" of a specimen has to be imaged. See, for example, the following reference:
  en.wikipedia.org/wiki/Cone beam computed tomography
A helical scan, in which the source follows a coil-like (spiral) path about a (longitudinal) axis of the specimen, and images are again captured at a relatively high sampling rate (i.e. quasi-continuously) along this path. This type of scan can be applied in situations where a relatively elongated portion of a specimen has to be imaged. It is typically achieved by combining circular motion (e.g. of the source) and concurrent translational motion (e.g. of the specimen). See, for example, the following reference:
  en.wikipedia.org/wiki/Spiral computed tomography
A "matrix" of sampling points, which are not disposed along a curve, but are instead arranged in a substantially uniform distribution. Such a scenario is set forth in co-pending European Patent Application EP15181202.1/U.S. patent application Ser. No. 15/237,309 (with the same assignee as the present application).

The beam of radiation that traverses the specimen can, for example, be regarded as being cone-like (thus yielding so-called (wide or narrow) cone beam tomography) or resembling a segment of a disc (thus yielding so-called fan beam tomography), depending on the geometry/shape that the detector "presents" to the source; alternatively, a parallel/collimated beam is also possible. The "line of sight" alluded to here can be regarded as corresponding to an "optical axis" along which the beam (from source through specimen to detector) propagates; it basically corresponds to the position of a central/median/core ray in that beam.

As regards the mathematical reconstruction technique used to produce a tomogram from a series of input images, use can be made of algorithms such as SIRT (Simultaneous Iterative Reconstruction Technique), ART (Algebraic Reconstruction Technique), DART (Discrete ART), SART (Simultaneous ART), MGIR (Multi-Grid Iterative Reconstruction), and many others: see, for example, the summary presented in the following publication:
  www.cs.toronto.edu/~nrezvani/CAIMS2009.pdf There are various known ways of generating X-rays, including, for example:
Using a synchrotron (high-energy synchrotron radiation).
Using a plasma discharge source, in which a microwave cavity or laser is used to vaporize a droplet of material, producing a high-energy plasma.
By bombarding a "heavy" target (e.g. a metallic body) with charged particles (e.g. electrons), causing production of Bremsstrahlung and characteristic/peak X-rays; this may occur in a transmissive or reflective configuration, as desired.

This latter method is conventionally used for X-ray tomography; the other methods are more exotic, and are more suitable for producing wavelength-specific X-rays, e.g. for EUV Lithography.

Tomographic imaging as referred to here can be performed using a standalone apparatus, which is conventionally the case in medical imaging applications, for example, where the specimen (e.g. a human or animal) is macroscopic. Standalone CT tools are also available for performing so-called "micro CT", in which a micro-focused source is used to image microscopic specimens, e.g. in geology/petrology, biological tissue studies, etc. Continuing this drive toward ever-greater resolution, so-called "nano CT" instruments have also been developed; these may be standalone tools, but, for example, they may also be embodied as (add-on) modules for (a vacant vacuum/interface port of) a charged-particle microscope (CPM), in which case the CPM's charged-particle beam is used to irradiate a (block-like) metal target, causing production of the X-rays used to perform the desired tomography. More information on (some) of these topics can, for example, be gleaned from the following references:
  en.wikipedia.org/wiki/X-ray microtomography en.wikipedia.org/wiki/Nanotomography www.ndt.net/article/dir2007/papers/24.pdf It should be noted that, as referred to here (inter alia) in the context of a CPM, the phrase "charged particle" should be broadly construed as encompassing:

Electrons, as in the case of a Transmission Electron Microscope (TEM), Scanning Electron Microscope (SEM), and Scanning Transmission Electron Microscope (STEM), for instance. See, for example, the following references:

en.wikipedia.org/wiki/Electron microscope en.wikipedia.org/wiki/Scanning electron microscope en.wikipedia.org/wiki/Transmission electron microscopy en.wikipedia.org/wiki/Scanning transmission electron microscopy Ions, which may be positive (e.g. Ga or He ions) or negative. Such ion beams can be used for imaging purposes, but they are also often used for surface modification purposes, e.g. as in the case of Focused Ion Beam (FIB) milling, Ion-Beam-Induced Deposition (IBID), Ion-Beam-Induced Etching (IBIE), etc. See, for example, the following references:

en.wikipedia.org/wiki/Focused ion beam en.wikipedia.org/wiki/Scanning Helium Ion Microscope W. H. Escovitz, T. R. Fox and R. Levi-Setti, *Scanning Transmission Ion Microscope with a Field Ion Source*, Proc. Nat. Acad. Sci. USA 72(5), pp 1826-1828 (1975).

Other charged particles, such as protons and positrons, for instance. See, for example, the following reference:

www.ncbi.nlm.nih.gov/pubmed/22472444

It should also be noted that, in addition to imaging and/or surface modification, a charged particle beam in a CPM may also have other functionalities, such as performing spectroscopy, examining diffractograms, etc.

Important aspects of the present invention relate to tomography as applied to image small (e.g. <ca. 10-20 mm width) and microscopic specimens, including specimens that are small/microscopic sub-portions of larger/macroscopic objects; it therefore is inter alia (but not exclusively) concerned with micro- and nano-CT techniques.

As set forth above, and as is well known to the skilled artisan, X-rays are conventionally produced by bombarding a target of metal (or other high-atomic-number material) with electrons (or other charged particles). Such X-ray production has worked relatively satisfactorily for macroscopic specimens, but more appropriate source architectures are being sought for use with small/microscopic specimens, as commonly studied using micro-CT and/or nano-CT, for example. The present invention concerns itself with such a novel source architecture.

It is an object of the invention to provide an innovative X-ray source for use in X-ray tomography, particularly in micro-CT and/or nano-CT, and also to provide an associated innovative tomographic method. More specifically, it is an object of the invention that said innovative source/method should inter alia be more versatile than what is currently known from the prior art, and should also be capable of achieving more satisfactory tomographic investigations, e.g. as regards attainable resolution.

These and other objects are achieved in a method as set forth in the opening paragraph above, characterized by:

Configuring said target to comprise a substrate of relatively low-atomic-number ("low-Z") material that carries an array of mutually isolated nuggets of a relatively high-atomic-number ("high-Z") material;

Selecting a particular one of said nuggets;

Performing step (b) by focusing said charged particle beam onto said selected nugget, without concurrently impinging upon another nugget.

Figure 3:
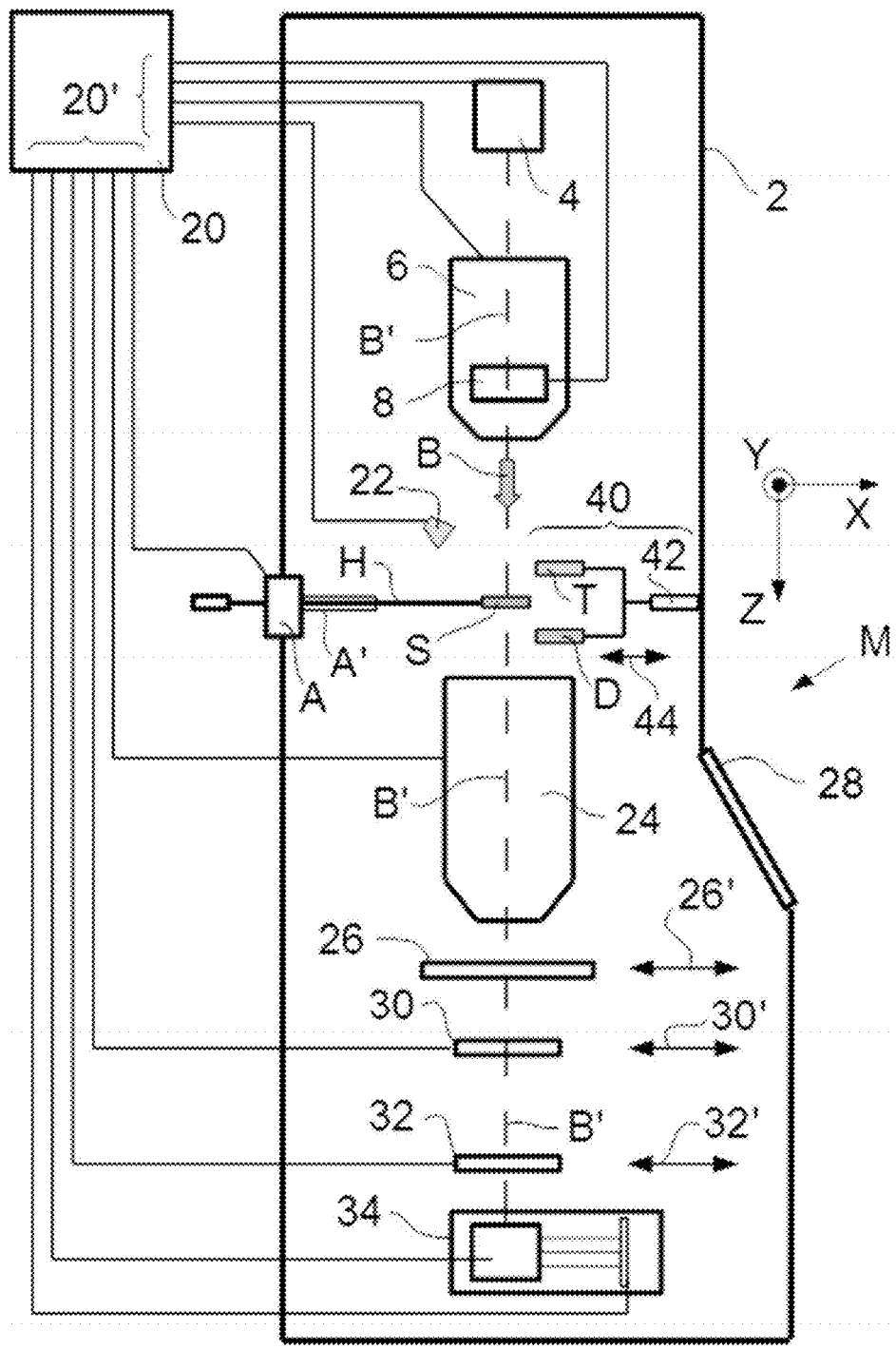
Figure 4:
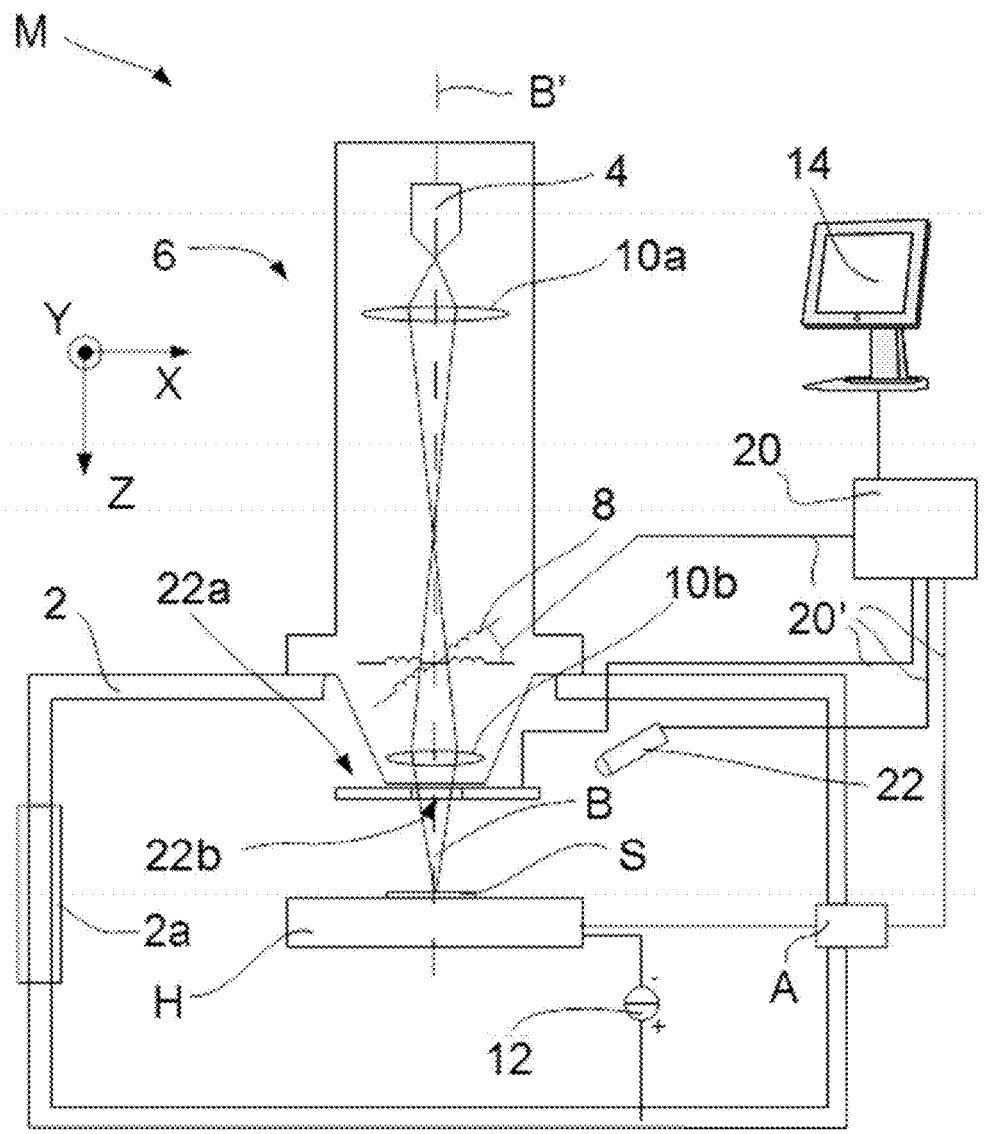
Figure 5:
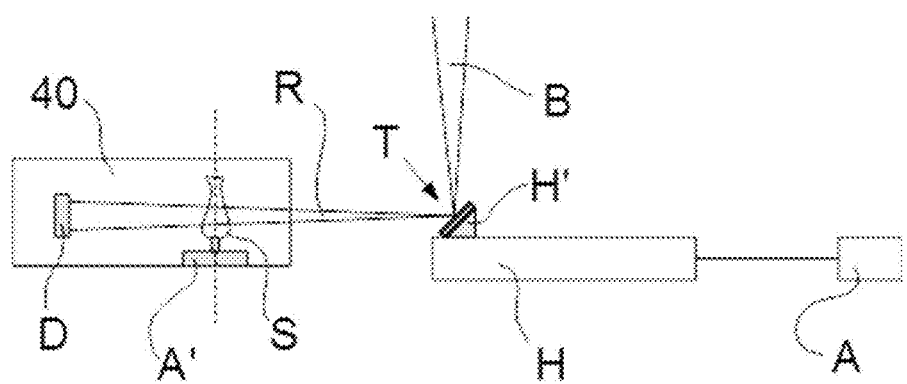

It should be noted that a target as specified here can be used in transmission (see, for example, FIGS. 1 and 3) or in reflection (see, for example, FIGS. 4 and 5). The skilled artisan will grasp that the phrases "relatively low" and "relatively high" as here employed are referenced to one another, e.g. the latter is relatively high compared to the former, and vice versa.

The invention achieves inter alia the following advantages:

The nuggets (lumps/grains) of material carried by the substrate can be made very small, e.g. of the order of only a few microns wide. Since only a single such nugget is irradiated at any time by the employed charged particle beam, the corresponding X-ray source will also be very small. Use of such a small X-ray source allows a significant increase in attainable imaging resolution.

Because high source brightness is also important, one will typically use a relatively high beam current in the employed charged particle beam. This will generally result in such a high thermal load on a given nugget that the nugget in question will typically "burn out" (melt/evaporate) in a relatively short time, e.g. after about a week of regular use. Rather than having to replace the entire X-ray target, the present invention allows the possibility of simply switching to a fresh nugget in the array. This can be done by using an actuator to move the substrate/array relative to the charged particle beam and/or by using a deflector to deflect the beam onto a different array node/nugget coordinate position on the substrate. This saves money (an X-ray target can cost several thousand dollars), and also saves time/improves accuracy by obviating the calibration procedure typically associated with a target swap-out. If desired, a lookup table can be used to store the coordinate positions (parallel to a substrate plane) of each of the (barycenters of the) nuggets, together with a lifetime indicator that records the cumulative radiation dose that a given nugget has received, allowing (automatic) flagging of the end-of-life (EOL) of a given nugget, and triggering selection of a fresh nugget.

Other significant advantages will now be discussed in the context of selected embodiments.

In a particular embodiment of the invention, the innovative X-ray target is configured such that at least two of said nuggets differ in respect of at least one property selected from the group comprising composition, size (e.g. cross-sectional area or thickness) and shape. Such an embodiment is advantageous in that—on a single target—different nuggets can be selectively invoked to satisfy different needs in different situations. For example:

If a first nugget comprises material A (such as tungsten, for example) and a second nugget comprises material B (such as molybdenum, for example), the X-ray spectrum from each of these nuggets will be different. This greatly facilitates spectral studies in a given tomographic apparatus, without having to do a target swap-out.

If a first nugget has a different density and/or size to a second nugget, this will allow different X-ray brightnesses to be achieved for a given charged particle beam current.

If a first nugget has a different size and/or shape to a second nugget, this will allow different source sizes/imaging resolutions to be achieved.

Once again, nugget selection can be effected by using an actuator to move the substrate/array relative to the charged particle beam and/or by using a deflector to deflect the beam onto a different array node/nugget coordinate position on the substrate. If desired, a lookup table can be used to store the coordinate positions (parallel to a substrate plane) of each of the (barycenters of the) nuggets, together with one or more entries concerning properties such as material, density, size, shape, etc.; in this way, a computer processor can be used to select a given nugget (or sequence of nuggets) during a measurement run, so as to execute a pre-programmed recipe and/or in response to selections made with the aid of a user interface.

In an embodiment of the invention, the following applies:

A surface of the employed substrate is provided with a thermally conductive coating, except at a number of uncoated surficial islands located on nodes of said array;

Each of said nuggets is disposed within a perimeter of a corresponding one of said islands.

The coating in question may, for example, comprise a metal, such as tungsten (e.g. deposited in a layer a few microns thick). Such a target architecture is advantageous in that it greatly facilitates conduction of heat away from an irradiated nugget, thereby helping to increase nugget life expectancy, and also helping to stabilize X-ray output from a given irradiated nugget. Furthermore, the coating can act as a screen/radiation shield around each nugget, serving to hinder extraneous/spurious radiation (e.g. generated by scattering within the employed particle-optical column) from reaching the specimen. A further advantage will be set forth in the next paragraph. If the coating is provided on the major surface of the substrate that faces toward the specimen, then it can be uniform, without the need to create islands therein; in that case, it will also act as a selective X-ray filter.

In another embodiment of the invention, a footprint (area) of the employed charged particle beam upon said substrate is selected to be larger than a footprint (presented to the irradiating beam) of the nugget being irradiated. Such a set-up allows a very spatially-confined X-ray source to be realized, since the nugget can be much smaller than the attainable "focal waist" of the employed charged particle beam. When using an embodiment as set forth in the previous paragraph, the beam footprint should preferably fit within the perimeter of the island within which the irradiated nugget is located. In such a scenario, one can conceive a beam centering mechanism whereby a beam offset is detected using, for example, a sensor that registers secondary radiation (such as backscattered electrons, secondary electrons, cathodoluminescence and/or X-rays) generated when a non-centered beam impinges on part of the coating rather than falling wholly within an island. If the employed sensor is segmented (e.g. as in the case of a quadrant detector), one can even effect auto-centering, whereby a control loop commands direction-specific relative motion of the irradiating beam and nugget until a signal from (one or more segments of) the detector has been nullified/balanced.

In the inventive X-ray target, it should be noted that the array of nuggets may be:

Deposited on a major surface of the carrier substrate. This can, for example, be done using (masked) physical vapor deposition, (masked) chemical vapor deposition, inkjet printing technology, silk screening, etc. It includes a situation whereby nuggets are disposed in hollows/depressions provided (e.g. etched) into said major surface. Or;

Embedded (partially or completely) within the substrate material. This can, for example, be achieved using a casting/molding technique, whereby nuggets are suspended in congealed substrate material.

In a particular embodiment of the invention utilizing the former of these scenarios, the substrate surface upon which the nuggets are deposited is oriented so as to face toward the specimen (rather than away from it), so that the nuggets are at a side of the substrate proximal to the specimen (rather than distal therefrom). This allows a smaller working distance to be achieved between the specimen and the actual X-ray source (the selected blob being irradiated with charged particles), with an attendant increase in imaging magnification. This is not a mandatory embodiment: one can instead flip the substrate so that the nuggets face away from the specimen, in which case the working distance will be increased by (at least) the thickness of the substrate. Corresponding considerations apply to a situation in which the nuggets are embedded within the substrate, but are nearer to a first major surface thereof than to an oppositely located second major surface.

As regards the array geometry according to which the nuggets are distributed across the substrate, this may, for example, include regular geometries such as orthogonal, sheared orthogonal, trigonal and hexagonal, or irregular/random geometries.

For guidance purposes, the following non-limiting example is presented:

Diameter of substrate: ca. 10-20 mm

Thickness of substrate: ca. 30-500 μm.

Material of substrate (low-Z): Diamond, graphene, Be, $Si_xN_y$, Si, $SiO_2$, etc.

Size of nuggets: ca. 0.1-10 μm wide, 0.3-30 μm thick/high.

Mutual average separation of nuggets: ~0.1-100 μm.

Material of nuggets (high-Z): W, Cu, Ti, Au, Ag, Rh, Mo, Fe, Cr, Co, Sc, etc., and also various alloys of these metals.

Focal waist/spot diameter of charged particle beam (on nuggets): ca. 0.1-20 μm.

The skilled artisan will not be bound by these examples, and will be able to tailor the parameters of the inventive X-ray target/source to suit the needs of a given situation.

The skilled artisan will appreciate that the present invention can be applied in a standalone CT apparatus, but is also suitable for application in a CT module in a TEM, STEM, SEM, FIB-SEM, and various other types of CPM, for example. It could also be incorporated as a CT module in an optical microscope, such as a confocal microscope, for example.

The invention will now be elucidated in more detail on the basis of exemplary embodiments and the accompanying schematic drawings, in which:

FIG. 1 renders a longitudinal cross-sectional view of an embodiment of a standalone X-ray tomography apparatus in which the present invention is implemented.

Figure 2:
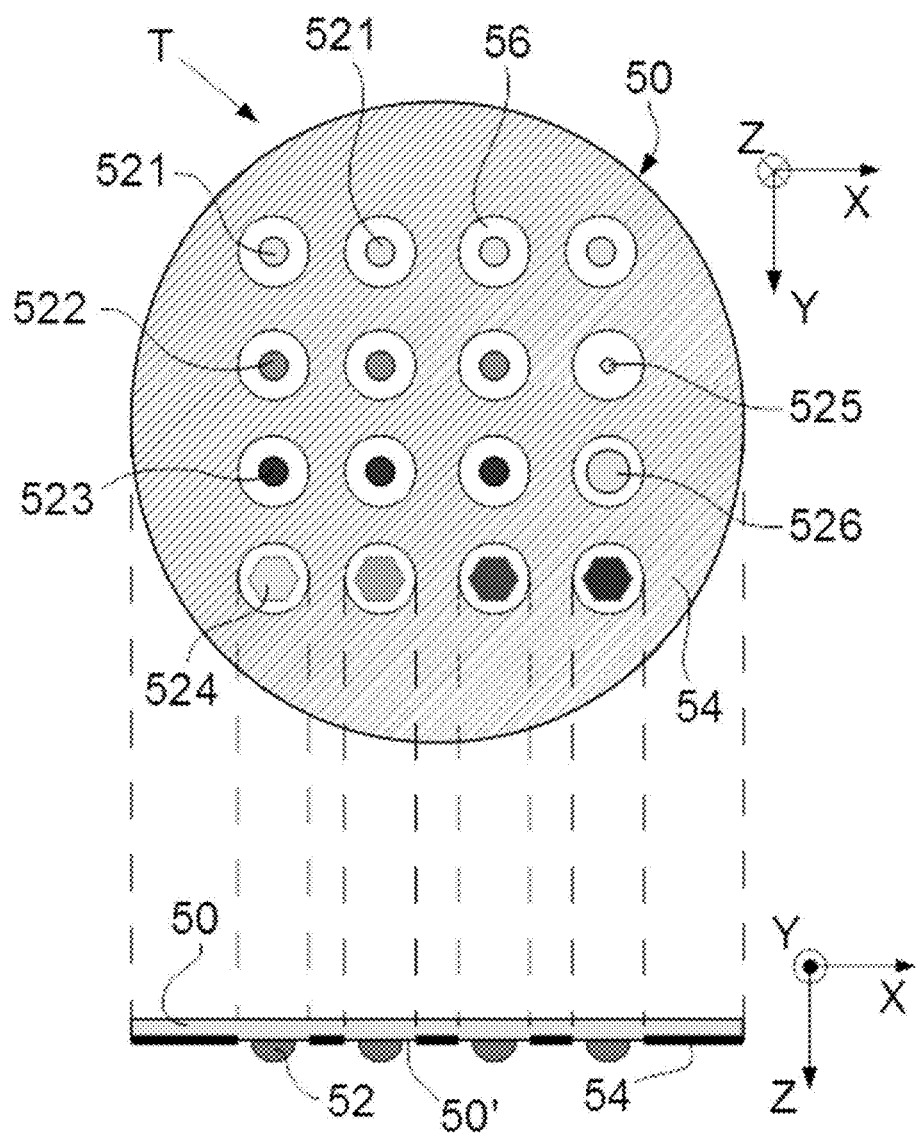

FIG. 2 shows a magnified view of a portion of FIG. 1, and depicts details of an X-ray target according to the present invention.

FIG. 3 renders a longitudinal cross-sectional view of an embodiment of a CPM (a (S)TEM) in which the present invention is implemented.

FIG. 4 renders a longitudinal cross-sectional view of a different embodiment of a CPM (a SEM) in which the present invention is implemented.

FIG. 5 illustrates a CT module suitable for use in a CPM such as that shown in FIG. 4.

In the Figures, where pertinent, corresponding parts are indicated using corresponding reference symbols.

Embodiment 1

FIG. 1 (not to scale) is a highly schematic depiction of an embodiment of a CT apparatus O in which the present invention is applied. The various items depicted in the Figure are as follows:

- A vacuum enclosure 2, which can be evacuated using suitable vacuum pumps.
- A charged particle source 4, such as a W, $LaB_6$, Schottky or Cold Field Emission Gun (CFEG) in the case of electrons, or a Liquid Metal Ion Source (LMIS) or Nano-Aperture Ion Source (NAIS) in the case of ions, for example. This produces a beam B of charged particles that propagate along particle-optical axis B'.
- An illuminator 6. In the present context, important functions of this illuminator 6 are to accelerate and focus the beam B, e.g. with the aid of a cascade arrangement of electrostatic acceleration electrodes. It may also, for example, comprise a beam deflector (to allow the beam B to be directed onto a chosen nugget).
- An X-ray target T, which (inter alia) comprises a body of relatively high-Z material (such as Au, W, Pt, etc.) onto which the beam B can be directed so as to produce a beam R of X-rays. This target T will typically be provided in a fitting that facilitates easy mounting/removal, e.g. for servicing/swapping purposes. Such a fitting may also allow movement of the target T in the XY plane (to allow a chosen nugget to be moved onto/off of axis B').
- A specimen holder H, connected to an actuator system A, for holding/positioning/moving a specimen S relative to said X-ray beam R, e.g. for rotating the specimen S about axis X and translating the specimen S parallel to axis X, so as to effect a helical scan.
- An X-ray detector D, such as a Silicon drift detector or Silicon-Lithium (SiLi) detector, for example. If desired, the detector D may comprises a scintillator, to convert X-rays to (visible) light prior to detection, and/or it may also comprise some X-ray optics prior to its radiation-sensitive element, for example.

Note that, because (relatively long-wavelength) X-rays are not strongly absorbed by air, the chamber portion 2' need not be evacuated; in such a situation, dividing wall 2" and the target T itself can form a vacuum barrier between portions 2 and 2'. It should also be noted that the apparatus O will generally comprise a controller/computer processor (not depicted), for controlling operation of various components in the apparatus.

Turning now to FIG. 2, this shows a highly magnified view of an embodiment of an X-ray (generating) target T in accordance with the present invention, both in plan view (upper portion of the Figure) and in elevation (lower portion of the Figure). Depicted is a substrate 50 of relatively low-atomic-number material (such as diamond, for example) that carries an array of mutually isolated nuggets 52 of a relatively high-atomic-number material (such as W, for example). In the present situation, the nuggets 52 take the form of blobs that are deposited upon a surface 50' of substrate 50 (e.g. using vapor deposition, silk screening, chemical deposition, lithography, etc.), though they could alternatively be (partially or completely) embedded within the body of substrate 50, for example. Also, in this particular case:

- The surface 50' is provided with a thermally conductive coating 54 (e.g. W, Mo, Ti or Cu, with a thickness of ca. 1-300 μm), except at a number of uncoated surficial islands 56 (e.g. with a diameter of ca. 0.3-100 μm) located on/at nodes of said array;
- Each of the nuggets/blobs 52 is disposed within a perimeter of an island 56, though such a layer 54 does not necessarily have to be employed. As here depicted, the target T is used "face down", i.e. with the nuggets/blobs 52 facing the specimen S/within the air enclosure 2', though this is purely a matter of choice; note, however, that such a "face down" arrangement allows the nuggets/blobs 52 to be located closer to the specimen S, thereby (inter alia) allowing a higher imaging magnification to be achieved upon detector D.

In this particular case, for illustration purposes, the nuggets/blobs are provided in a variety of different compositions, sizes and shapes—though one can also choose a more "monotonic"/uniform embodiment, if desired. For example:

- Nuggets 521, 522 and 523 are of the same shape (round) and size (e.g. ca. 1 micron in diameter), but comprise different materials (e.g. W, Ti and Mo respectively).
- Nuggets 521, 525 and 526 are of the same shape and composition, but have different sizes [widths (normal to Z) and/or thicknesses (parallel to Z)] (e.g. ca. 1, 0.3 and 10 microns wide).
- Nugget 524 has a different shape (e.g. hexagonal) to that of nugget 526 (round), though it has approximately the same area and composition.

The charged particle beam B focused on the nuggets 52 may, for example, have a spot size of the order of ca. 0.3 microns (this will depend inter alia on the size of the particular nugget being irradiated) and a beam current of the order of ca. 1-50 μA. The separation between the target T and specimen S may, for example, be of the order of ca. 0.05-0.2 mm.

Embodiment 2

FIG. 3 (not to scale) is a highly schematic depiction of an embodiment of a charged-particle microscope M in which the present invention can be implemented; more specifically, it shows an embodiment of a transmission-type microscope M, which, in this case, is a TEM/STEM (though, in the context of the current invention, it could just as validly be a SEM (see FIG. 4), or an ion-based microscope, for example). In the Figure, within a vacuum enclosure 2, an electron source 4 produces a beam B of electrons that propagates along an electron-optical axis B' and traverses an electron-optical illuminator 6, serving to direct/focus the electrons onto a chosen part of a specimen S (which may, for example, be (locally) thinned/planarized). Also depicted is a deflector 8, which (inter alia) can be used to effect scanning motion of the beam B.

The specimen S is held on a specimen holder H that can be positioned in multiple degrees of freedom by a positioning device/stage A, which moves a cradle A' into which holder H is (removably) affixed; for example, the specimen holder H may comprise a finger that can be moved (inter alia) in the XY plane (see the depicted Cartesian coordinate system; typically, motion parallel to Z and tilt about X/Y will also be possible). Such movement allows different parts of the specimen S to be illuminated/imaged/inspected by the electron beam B traveling along axis B' (in the Z direction)

(and/or allows scanning motion to be performed, as an alternative to beam scanning). If desired, an optional cooling device (not depicted) can be brought into intimate thermal contact with the specimen holder H, so as to maintain it (and the specimen S thereupon) at cryogenic temperatures, for example.

The electron beam B will interact with the specimen S in such a manner as to cause various types of "stimulated" radiation to emanate from the specimen S, including (for example) secondary electrons, backscattered electrons, X-rays and optical radiation (cathodoluminescence). If desired, one or more of these radiation types can be detected with the aid of analysis device 22, which might be a combined scintillator/photomultiplier or EDX (Energy-Dispersive X-Ray Spectroscopy) module, for instance; in such a case, an image could be constructed using basically the same principle as in a SEM. However, alternatively or supplementally, one can study electrons that traverse (pass through) the specimen S, exit/emanate from it and continue to propagate (substantially, though generally with some deflection/scattering) along axis B'. Such a transmitted electron flux enters an imaging system (projection lens) 24, which will generally comprise a variety of electrostatic/magnetic lenses, deflectors, correctors (such as stigmators), etc. In normal (non-scanning) TEM mode, this imaging system 24 can focus the transmitted electron flux onto a fluorescent screen 26, which, if desired, can be retracted/withdrawn (as schematically indicated by arrows 26') so as to get it out of the way of axis B'. An image (or diffractogram) of (part of) the specimen S will be formed by imaging system 24 on screen 26, and this may be viewed through viewing port 28 located in a suitable part of a wall of enclosure 2. The retraction mechanism for screen 26 may, for example, be mechanical and/or electrical in nature, and is not depicted here.

As an alternative to viewing an image on screen 26, one can instead make use of the fact that the depth of focus of the electron flux leaving imaging system 24 is generally quite large (e.g. of the order of 1 meter). Consequently, various other types of analysis apparatus can be used downstream of screen 26, such as:

TEM camera 30. At camera 30, the electron flux can form a static image (or diffractogram) that can be processed by controller/processor 20 and displayed on a display device (not depicted), such as a flat panel display, for example. When not required, camera 30 can be retracted/withdrawn (as schematically indicated by arrows 30') so as to get it out of the way of axis B'.

STEM camera 32. An output from camera 32 can be recorded as a function of (X,Y) scanning position of the beam B on the specimen S, and an image can be constructed that is a "map" of output from camera 32 as a function of X,Y. Camera 32 can comprise a single pixel with a diameter of e.g. 20 mm, as opposed to the matrix of pixels characteristically present in camera 30. Moreover, camera 32 will generally have a much higher acquisition rate (e.g. $10^6$ points per second) than camera 30 (e.g. $10^2$ images per second). Once again, when not required, camera 32 can be retracted/withdrawn (as schematically indicated by arrows 32') so as to get it out of the way of axis B' (although such retraction would not be a necessity in the case of a donut-shaped annular dark field camera 32, for example; in such a camera, a central hole would allow flux passage when the camera was not in use).

As an alternative to imaging using cameras 30 or 32, one can also invoke spectroscopic apparatus 34, which could be an EELS module, for example.

It should be noted that the order/location of items 30, 32 and 34 is not strict, and many possible variations are conceivable. For example, spectroscopic apparatus 34 can also be integrated into the imaging system 24.

Note that the controller (computer processor) 20 is connected to various illustrated components via control lines (buses) 20'. This controller 20 can provide a variety of functions, such as synchronizing actions, providing setpoints, processing signals, performing calculations, and displaying messages/information on a display device (not depicted). Needless to say, the (schematically depicted) controller 20 may be (partially) inside or outside the enclosure 2, and may have a unitary or composite structure, as desired.

The skilled artisan will understand that the interior of the enclosure 2 does not have to be kept at a strict vacuum; for example, in a so-called "Environmental TEM/STEM", a background atmosphere of a given gas is deliberately introduced/maintained within the enclosure 2. The skilled artisan will also understand that, in practice, it may be advantageous to confine the volume of enclosure 2 so that, where possible, it essentially hugs the axis B', taking the form of a small tube (e.g. of the order of 1 cm in diameter) through which the employed electron beam passes, but widening out to accommodate structures such as the source 4, specimen holder H, screen 26, camera 30, camera 32, spectroscopic apparatus 34, etc.

In the particular context of the present invention, the microscope M comprises a retractable X-ray CT module 40, which can be advanced/withdrawn with the aid of positioning system 42 so as to place it on/remove it from the path of the beam B (see arrow 44). In the particular configuration illustrated here, the module 40 comprises a fork-like frame on which are mounted:

A target T, above the plane of the specimen S.

An X-ray detector D, below the plane of the specimen S.

The target T is configured according to the present invention, and may have a structure similar to that illustrated in FIG. 2, for example.

Embodiment 3

FIG. 4 (not to scale) is a highly schematic depiction of a different embodiment of a charged-particle microscope M in which the present invention can be implemented; more specifically, it shows an embodiment of a non-transmission-type microscope M, which, in this case, is a SEM (though, in the context of the current invention, it could just as validly be an ion-based microscope, for example). In the Figure, parts which correspond to items in FIG. 3 are indicated using identical reference symbols, and will not be separately discussed here. Additional to FIG. 3 are (inter alia) the following parts:

2a: A vacuum port, which may be opened so as to introduce/remove items (components, specimens) to/from the interior of vacuum chamber 2, or onto which, for example, an ancillary device/module 40 may be mounted (see FIG. 5, for example). The microscope M may comprise a plurality of such ports 2a, if desired.

10a, 10b: Schematically depicted lenses/optical elements in illuminator 6.

12: A voltage source, allowing the specimen holder H, or at least the specimen S, to be biased (floated) to an electrical potential with respect to ground, if desired.

14: A display, such as a FPD or CRT.

22a, 22b: A segmented electron detector 22a, comprising a plurality of independent detection segments (e.g. quadrants) disposed about a central aperture 22b (allowing passage of the beam B). Such a detector can, for example, be used to investigate (the angular dependence of) a flux of output (secondary or backscattered) electrons emerging from the specimen S.

Turning now to FIG. 5, this shows an in situ CT module 40. In this Figure, the CPM's specimen holder H has been provided with:

A canting block H', with an angled mounting face;

A target T in accordance with the present invention, which is positioned (using actuator A) so that electron beam B impinges upon it, thus producing X-rays in a variety of directions. The Figure shows a beam R of such X-rays that propagate to one side from target T into module 40, where they pass through a specimen S and impinge upon detector D. The specimen S is mounted on a stage apparatus A' that allows the specimen S to be positioned/moved (typically translated and rotated) relative to the target T.

Such a CT module 40 may be permanently present (ab initio) in the vacuum enclosure 2, or it may be an add-on module that can be mounted (post-manufacture of the CPM M) on/within a spare vacuum port 2a, for example.

The invention claimed is:

1. A method of investigating a specimen using X-ray tomography, comprising:
    (a) mounting the specimen to a specimen holder;
    (b) providing an X-ray source, in which X-rays are generated by irradiating a target with a charged particle beam;
    (c) using said X-ray source to illuminate the specimen with a beam of X-rays along a first line of sight through the specimen, detecting a flux of X-rays transmitted through the specimen and forming a first image therewith;
    (d) repeating step (c) for a series of different lines of sight through the specimen, thereby producing a corresponding series of images;
    (e) performing a mathematical reconstruction on said series of images, so as produce a tomogram of at least part of the specimen;
    (f) configuring said target to comprise a substrate of relatively low-atomic-number material that carries an array of mutually isolated nuggets of a relatively high-atomic-number material, wherein a surface of said substrate is provided with a thermally conductive coating, except at a number of uncoated surfacial islands located on nodes of said array, and each of said nuggets is disposed within a perimeter of a corresponding one of said islands;
    (g) selecting a particular one of said nuggets; and
    (h) performing step (c) by focusing said charged particle beam onto said selected nugget, without concurrently impinging upon another nugget.

2. The method according to claim 1, wherein said target is configured such that at least two of said nuggets differ in respect of at least one property selected from the group comprising composition, size and shape.

3. The method according to claim 2, wherein:
    in a first measurement session, step (c) is performed using a first of said nuggets; and
    in a second measurement session, step (c) is performed using a second of said nuggets.

4. The method according to claim 3, wherein a surface of the substrate facing toward the specimen is uniformly covered with said thermally conductive coating.

5. The method according to claim 2, wherein said nuggets are deposited upon a surface of said substrate.

6. The method according to claim 2, wherein said nuggets are embedded within said substrate.

7. The method according to claim 2, wherein at least some nuggets are located closer to a first surface of the substrate than to an oppositely located second surface; and the substrate is oriented so that said first surface faces toward the specimen.

8. The method according to claim 2, wherein a footprint of said charged particle beam upon said substrate is selected to be larger than a footprint of said selected nugget.

9. The method according to claim 1, wherein said nuggets are deposited upon a surface of said substrate.

10. The method according to claim 1, wherein said nuggets are embedded within said substrate.

11. The method according to claim 1, wherein at least some nuggets are located closer to a first surface of the substrate than to an oppositely located second surface; and the substrate is oriented so that said first surface faces toward the specimen.

12. The method according to claim 1, wherein a surface of the substrate facing toward the specimen is uniformly covered with said thermally conductive coating.

13. The method according to claim 1, wherein a footprint of said charged particle beam upon said substrate is selected to be larger than a footprint of said selected nugget.

14. A tomographic apparatus comprising:
    a specimen holder, for holding a specimen;
    a charged particle column, for producing a charged particle beam;
    an X-ray source, for illuminating the specimen with a beam of X-rays, produced by irradiating a target with said charged particle beam;
    a detector, for detecting a flux of X-rays transmitted through the specimen and forming an image therefrom;
    a controller, configured to:
    repeat said detection and imaging for a series of different lines of sight through the specimen, thereby producing a corresponding series of images; and
    perform a mathematical reconstruction on said series of images, so as produce a tomogram of at least part of the specimen;
    wherein
    said target comprises a substrate of relatively low-atomic-number material that carries an array of mutually isolated nuggets of a relatively high-atomic-number material, a surface of said substrate is provided with a thermally conductive coating, except at a number of uncoated surfacial islands located on nodes of said array, and each of said nuggets is disposed within a perimeter of a corresponding one of said islands;
    wherein said controller is configured to:
        select coordinates of a particular one of said nuggets; and
        produce said X-ray beam by focusing said charged particle beam onto said selected nugget, without concurrently impinging upon another nugget.

15. A charged particle microscope comprising a tomographic apparatus as claimed in claim 14.

16. The tomographic apparatus according to claim 14, wherein a surface of the substrate facing toward the specimen is uniformly covered with said thermally conductive coating.

* * * * *